United States Patent [19]

Nap et al.

[11] Patent Number: 5,897,536
[45] Date of Patent: Apr. 27, 1999

[54] CATHETER HAVING A CONTROLLABLE STIFFNESS AND ADAPTED FOR USE WITH VARIOUS CONTRAST MEDIA

[75] Inventors: Cornelis Philipus Nap, Zevenhuizen; Frans Mous, Drachten; Wenzel Franz Hurtak, Roden, all of Netherlands

[73] Assignee: Cordis Europa, N.V., Netherlands

[21] Appl. No.: 08/936,051

[22] Filed: Sep. 23, 1997

[30] Foreign Application Priority Data

Sep. 24, 1996 [NL] Netherlands ............................ 1004102

[51] Int. Cl.$^6$ .................................................. A61M 25/00
[52] U.S. Cl. .......................................... 604/280; 604/264
[58] Field of Search .................................. 604/264, 256, 604/280, 282

[56] References Cited

U.S. PATENT DOCUMENTS 2,548,602  4/1951  Greenburg .
4,096,862  6/1978  DeLuca .
5,034,005  7/1991  Appling .
5,464,023  11/1995  Viera .

FOREIGN PATENT DOCUMENTS 2 044 109  3/1980  United Kingdom .

*Primary Examiner*—John D. Yasko
*Assistant Examiner*—Deborah Blyveis
*Attorney, Agent, or Firm*—Michael W. Montgomery

[57] ABSTRACT

An intravascular catheter having controllable stiffness or flexibility, and adapted for use with various contrast media. The stiffness of the catheter may be increased during the use of the catheter by applying a fluid under pressure at the proximal end of the catheter to thereby fill a cavity within the body of the catheter to thereby cause the region of the catheter defined by the cavity to become less flexible. When the fluid pressure is decreased, this region of the catheter becomes more flexible. The fluids to be applied inside the cavities may be a variety of types of contrast media, used with imaging techniques such as either MRI or X-ray fluoroscopy.

6 Claims, 1 Drawing Sheet

CATHETER HAVING A CONTROLLABLE STIFFNESS AND ADAPTED FOR USE WITH VARIOUS CONTRAST MEDIA

BACKGROUND AND SUMMARY OF THE INVENTION

The present invention relates to a catheter for use within the vasculature of the human body, and, more particularly, concerns a catheter in which the stiffness, or flexibility, may be controlled during the use thereof.

Medical devices such as intravascular catheters, and the like, are placed into various body orifices for many purposes, including the infusion of fluids, withdrawal of fluid samples from the body, and for the insertion of angiography balloons. Very often, such a device has to be placed in a remote part of the body, or perhaps threaded for a considerable distance through the vascular system. Most catheters of the type designed for placement into a deep body position are made of pliable, very flexible, plastic material. Such material facilitates any bending or curving that may be necessary during placement and also serves to eliminate or decrease the traumatic effect of the insertion of the medical device. However, the relatively low flexural modulus of most catheters which provides the pliable nature of the catheter often produces difficulties in controlling the catheter as it is passed through the vascular system.

One problem which arises using most of the very flexible catheters during insertion into the vessels is the tendency of the catheter to bend and flex during the insertion stage. This action produces awkward and erratic threading of the catheter by the operator. This problem can become acute when the catheter is long and is intended to be positioned deep within the vasculature of the patient.

Catheters have employed fluid pressurization to accomplish various functions. For example, U.S. Pat. No. 3,525,329 discloses an evertable, extensible probe which when pressurized extends the probe into the body cavity to be examined. U.S. Pat. No. 3,502,069 employs a rigid tubular casing and a flexible evertable tubing inside. When fluid pressure is applied to the casing the tubing is everted out of an open end of the casing. U.S. Pat. No. 3,168,092 describes a probing instrument with a tubing which becomes extraverted under pressure, whereby the tubing exerts pressure on the walls of the cavity to separate the walls thereof.

Accordingly, it is most desirable to employ a catheter, or like instrument, which has a certain level of stiffness in order to facilitate placement of the catheter with relative ease within the vascular system of a patient. However, as pointed out above, after placement of the catheter well into the vasculature, the initial level of stiffness is undesirable since more pliability and flexibility may be required. It can be seen, then, that it is desirable to be able to vary the degree of stiffness of the catheter so as to have a relatively high degree of stiffness during placement of the catheter into the patient and then a relatively low degree of stiffness for final positioning.

A catheter having a variable flexibility, or flexural modulus, for insertion into a body comprises a length of flexible tubing having a normally relatively low flexural modulus. A lumen inside the tubing provides a free flow path therethrough. A fluid control system is associated with the tubing for controllably increasing the flexural modulus of the tubing to stiffen the same during insertion of the tubing into the body. After being positioned in the body, the fluid control system is adjusted to allow the tubing to return to its normally relatively low flexural modulus.

In the preferred embodiment of this aspect of the invention, the means for increasing the flexural modulus of the tubing includes a lumen associated with the catheter tubing. This lumen is coupled to one or more fluid cavities within the catheter tubing and to a pressure source. An increase in pressure in the lumen serves to increase the flexural modulus of the catheter tubing at one or more regions defined by the cavities with the pressure being controllable so that the flexural modulus of the catheter is also controllable. This lumen may be a second tube located within the catheter tubing.

In accordance with the principles of the present invention, the catheter advantageously offers the desirable stiffness characteristic during the placement or insertion stage into the body, while also providing the ability to reduce the stiffness after final positioning so that the catheter may be pliant and flexible for final positioning. Accordingly, the catheter, or like instrument, of the present invention allows the operator to manipulate the catheter into the patient with relative ease and substantially eliminates, or reduces, the awkwardness which accompanies the insertion of catheters which do not have the variable stiffness feature.

There is provided a catheter according to the invention for use within the vasculature of the human body comprising a flexible outer cylindrical tubing having an inner lumen and proximal and distal ends, a first cylindrical sealing plug positioned within the lumen of the cylindrical tubing at the distal end of the tubing, a second cylindrical sealing plug positioned within the lumen of the cylindrical tubing and spaced apart at a predetermined distance proximally from the first sealing plug so as to define a cavity between the first and second sealing plugs, a fluid passageway extending through the second sealing plug, and connector means connected to the proximal end of the catheter and having a lumen which is in fluid communication with the passageway of the second sealing plug so that fluid under pressure may be applied to the connector means to fill the cavity between the first and second sealing plugs to thereby stiffen the catheter in a region between the first and second sealing plugs.

Also, the catheter preferably includes a cylindrical spacer disposed between the first and second sealing plugs to maintain the predetermined distance between the sealing plugs.

Still further, the cylindrical spacer has a central axis which is coaxial with the central axis of the first and second sealing plugs and the outside diameter of the cylindrical spacer is less than the diameter of the inner lumen of the cylindrical tubing of the catheter.

In addition, preferably the passageway which extends through the second sealing plug is defined by the wall of a longitudinal slot which extends through the second sealing tube and an adjacent portion of the wall of the inner lumen of the cylindrical tubing of the catheter.

Still further, the catheter includes a guidewire lumen which extends through and is coaxial to the central axis of the first cylindrical sealing plug, the cylindrical spacer and the second cylindrical sealing plug to thereby provide a guidewire lumen which is coaxial with the flexible outer tubing of the catheter.

In addition, the catheter includes a flexible guidewire slidably received by the guidewire lumen.

Further, the catheter includes a third cylindrical sealing plug positioned within the lumen of the cylindrical tubing and spaced apart at a predetermined distance from the second cylindrical sealing plug so as to define a second cavity between the second and third sealing plugs, and a fluid passageway extending through the third sealing plug and being in communication with the lumen of the connector means so that fluid pressure may be applied to the connector means to fill the cavities between the first and second sealing plugs and between the second and third sealing plugs to thereby stiffen the regions between the respective sealing plugs.

There is provided a catheter according to the invention is such that the cavity is ring-shaped. In this case the cavity has been arranged so as to surround the guidewire lumen.

There is also provided a catheter according to this invention in which the guidewire lumen may be used for other purposes, such as conveying a fluid through the catheter or for receiving a glass fibre cable.

Still further there is provided a catheter according to this invention which the passageway may be used to fill the cavity with a fluid such as a contrast medium, air or another liquid which may later be removed from the cavity.

The fluids to be applied inside the cavities may for instance be a contrast medium, used with imaging techniques such as MRI or when using X-radiation, air or a resin curing under the influence of visible or UV-light.

BRIEF DESCRIPTION OF THE DRAWINGS

The invention will be explained in greater detail below with reference to the attached drawings of an embodiment thereof.

DESCRIPTION OF A PREFERRED EMBODIMENT

Figures 1, 2:
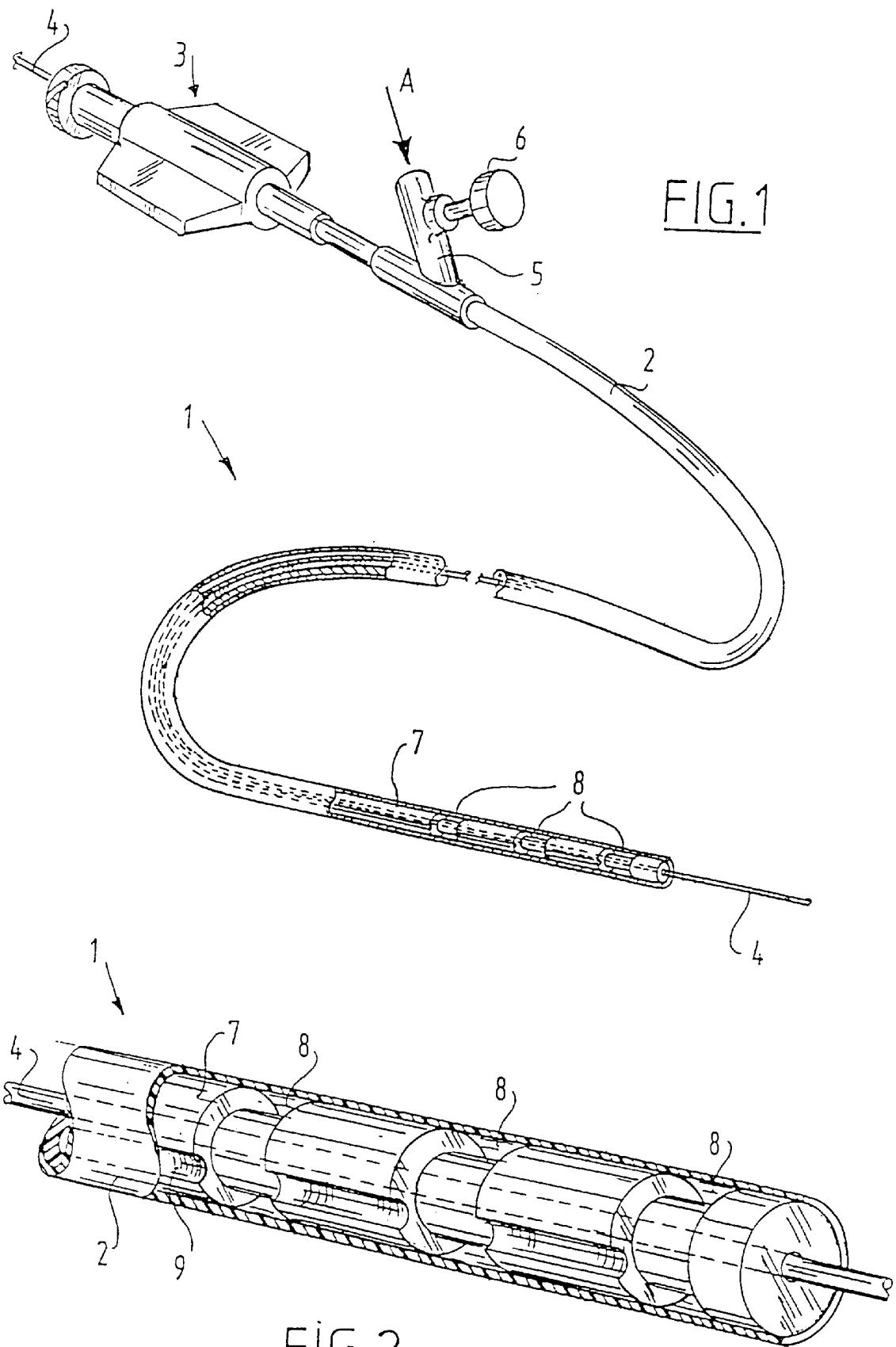
FIG. 1 shows a perspective view of a catheter according to this invention.
FIG. 2 shows a cut-away perspective view of a section of the catheter illustrated in FIG. 1.

A preferred embodiment of the present invention is shown in FIG. 1 in which the catheter comprises a tubular basic body in the shape of a hollow tube 2, a connecting member in the shape of a handle 3, and a tubular member in the shape of a filling body 7.

A guidewire 4 is inserted through the handle 3, and is advanced over the entire length of the catheter 1 through the hollow tube 2. The guidewire 4, takes the form of a glass fiber cable, also passes through the inside of the filling body 7 which has been illustrated in greater detail in FIG. 2.

It should be noted that the filling body 7 has a varying thickness, so that cavities 8 have been formed in between the filling body and the inside of the tube 2. The filling body also comprises an additional lumen shaped like a channel through which the glass fibre cable 4 has been inserted.

The cavities, which can be seen most clearly in FIG. 2, are connected to a connecting member in the shape of a Y-piece 5, which can be closed by means of the control means 6, in the open state of which fluid can be conveyed to the cavities 8 in the direction of the arrow A. A fluid to be transported to the cavity 8 may for instance be a contrast medium, whereby the distance between the separate cavities 8 is known in advance, so that when an image is created of the vicinity of the catheter 1 using X-radiation or an MRI-technique, the contrast medium designed for this purpose will be clearly visible, which will be helpful when interpreting the images because the distances between the cavities 8 are known beforehand. Furthermore, a fluid under pressure can be conveyed to the cavities 8 in order to increase the stiffness of the section of the catheter in which the cavities 8 have been arranged. In the case of another shape than the annular shape of the cavities 8 illustrated here, also bending of this section of the catheter can be effected at any time during its use, which can also be neutralized again when it is no longer necessary, by reducing the pressure in the cavities 8. In addition, the same is true when contrast medium has been arranged inside the cavities 8, that is to say, it can be removed from the cavities again via the same route. Preferably a return lumen, not illustrated, has been arranged for this transport to and from the cavities 8, so that air or another liquid can take the place of the contrast medium or the fluid under pressure or vice versa, without having to open up a connection with the direct surroundings of the catheter.

In FIG. 2 a cut-away perspective view is shown of the tube 2 illustrated in FIG. 1, inside of which the filling body 7 has been arranged. The addition lumen and/or the return lumen have in this case been formed by parallel grooves 9 arranged, substantially in the longitudinal direction of the catheter, in the thicker sections of the filling body 7, the circumference of which thicker sections correspond as such to the cross-section of the tube 2, inside of which the filling body has been arranged.

By way of addition or as an alternative also other shapes of cavities than the annular cavities 8 described above and illustrated in the drawings can be employed. Spiral shaped cavities, winding cavities, circular cavities or drop shaped cavities may be used for example. This summing up is not exhaustive however; many other shapes may be employed. Particular attention should also be paid to asymmetric shapes, which serve to cause bending of the catheter 1 when the fluid is supplied to the cavities.

Although only air and liquid have been referred to above by way of fluids, gasses other than air may be used. Furthermore, separate cavities may have been provided with corresponding additional lumens, and if desired also return lumens. As a result it will be possible to provide groups of cavities, which groups have been arranged dispersed around the circumference for the lumen, with for instance a gas under pressure in order to bend first in one direction and later in an opposite direction.

Providing catheters with cavities offers in addition many other advantages, and they may have any number of shapes and may be arranged in a catheter in many different ways.

Various other modifications in the arrangement of elements or in the configuration of elements and in the details of construction of the catheter without departing from the spirit and scope of the invention.

That which is claimed is:

1. A catheter for use within the vasculature of the human body, comprising:
    a flexible outer cylindrical tubing having an inner lumen and proximal and distal ends,
    a first substantially cylindrical sealing plug positioned within the lumen of the cylindrical tubing at the distal end of the tubing,
    a second substantially cylindrical sealing plug positioned within the lumen of the cylindrical tubing and spaced apart at a predetermined distance proximally from said first sealing plug, so as to define a cavity between the first and second sealing plugs,
    a substantially cylindrical spacer disposed between said first and second sealing plugs to maintain the predetermined distance between the sealing plugs,
    a fluid passageway extending through the second sealing plug, and connector means connected to the proximal end of the catheter and having a lumen which is in fluid communication with the passageway of the second sealing plug, so that a contrast fluid under pressure may be applied to the connector means to fill the cavity between the first and second sealing plugs to thereby stiffen the catheter in a region between the first and second sealing plugs, wherein the contrast fluid is selected from a group consisting essentially of contrast media visible under either fluoroscopy or magnetic resonance imaging.

2. A catheter as defined in claim 1, wherein the substantially cylindrical spacer has a central axis which is coaxial with the central axis of the first and second sealing plugs, and the outside diameter of the substantially cylindrical spacer is less than the diameter of the inner lumen of the cylindrical tubing of the catheter.

3. A catheter as defined in claim 2, wherein the passageway which extends through the second sealing plug is defined by the wall of a longitudinal slot which extends through the second sealing tube and an adjacent portion of the wall of the inner lumen of the cylindrical tubing of the catheter.

4. A catheter as defined in claim 3, further comprising a guidewire lumen which extends through and is coaxial to the central axis of the first cylindrical sealing plug, the cylindrical spacer, and the second cylindrical sealing plug to thereby provide a guidewire lumen which is coaxial with the flexible outer tubing of the catheter.

5. A catheter as defined in claim 4, including a flexible guidewire slidably received by the guidewire lumen.

6. A catheter as defined in claim 2, further comprising a third cylindrical sealing plug positioned within the lumen of the cylindrical tubing and being spaced apart at a predetermined distance from the second cylindrical sealing plug, so as to define a second cavity between the second and third sealing plugs, and a fluid passageway extending through the third sealing plug and being in communication with the lumen of the connector means, so that a contrast fluid under pressure may be applied to the connector means to fill the cavities between the first and second sealing plugs as well as between the second and third sealing plugs, to thereby stiffen the regions between the respective sealing plugs and cause the cavities to become visible under a medical imaging technology selected from the group of fluoroscopy and magnetic resonance imaging, wherein the contrast fluid is selected from a group consisting essentially of contrast media visible under either fluoroscopy or magnetic resonance imaging.

\* \* \* \* \*